United States Patent
Moreno Sierra et al.

(10) Patent No.: US 12,065,929 B2
(45) Date of Patent: Aug. 20, 2024

(54) PETRO-STEERING METHODOLOGIES DURING UNDER BALANCED COILED TUBING (UBTC) DRILLING OPERATIONS

(71) Applicant: Saudi Arabian Oil Company, Dhahran (SA)

(72) Inventors: Ferney Geovany Moreno Sierra, Dhahran (SA); Ahmad Azly Bin Abdul Aziz, Dhahran (SA); Neil W. Craigie, Dhahran (SA); Faisal S. Al Reshedan, Dammam (SA); Nawaf Aldossary, Dammam (SA)

(73) Assignee: Saudi Arabian Oil Company, Dhahran (SA)

( * ) Notice: Subject to any disclaimer, the term of this patent is extended or adjusted under 35 U.S.C. 154(b) by 29 days.

(21) Appl. No.: 17/647,814

(22) Filed: Jan. 12, 2022

(65) Prior Publication Data
US 2023/0221267 A1    Jul. 13, 2023

(51) Int. Cl.
| | |
|---|---|
| *E21B 7/04* | (2006.01) |
| *E21B 44/00* | (2006.01) |
| *G01N 23/20* | (2018.01) |
| *G01N 23/223* | (2006.01) |
| *G01N 33/24* | (2006.01) |

(52) U.S. Cl.
CPC ............... *E21B 7/04* (2013.01); *E21B 44/00* (2013.01); *G01N 23/20* (2013.01); *G01N 23/223* (2013.01); *G01N 33/24* (2013.01); *E21B 2200/20* (2020.05); *G01N 2223/05* (2013.01); *G01N 2223/076* (2013.01); *G01N 2223/616* (2013.01)

(58) Field of Classification Search
CPC ...... E21B 2200/20; E21B 44/00; G01N 33/24
See application file for complete search history.

(56) References Cited

U.S. PATENT DOCUMENTS

| | | | |
|---|---|---|---|
| 4,541,490 A | 9/1985 | Bigbie et al. | |
| 5,076,356 A | 12/1991 | Reimert | |
| 6,491,108 B1 | 12/2002 | Slup et al. | |
| 6,754,588 B2 | 6/2004 | Cross et al. | |
| 6,823,298 B1 | 11/2004 | Jones | |
| 7,606,666 B2 | 10/2009 | Repin et al. | |
| RE41,508 E | 8/2010 | Treece | |
| 7,828,060 B2 | 11/2010 | Churchill | |
| 7,881,155 B2 | 2/2011 | Close | |

(Continued)

FOREIGN PATENT DOCUMENTS

| | | |
|---|---|---|
| WO | WO 2016101374 | 6/2016 |
| WO | WO 2021231535 | 11/2021 |

OTHER PUBLICATIONS

Li et al., "Study on Pressure Measuring and Formation Evaluation Methods While Underbalanced Drilling," SPE/IADC 148438, presented at the SPE/IADC Middle East Drilling Technology Conference and Exhibition, Muscat, Oman, Oct. 2011, 8 pages.

Abaltusov et al., "The use of geosteering to achieve the drilling targets in multilateral fishbone wells in Russkoye Field," Abu Dhabi International Petroleum Exhibition & Conference, Nov. 2019, 14 pages.

Al-Omair et al., "Enhanced Sustained Production from Successful Underbalanced Coiled Tubing Drilling in Saudi Arabian Deep Tight Gas Sandstone and Carbonate Formations," SPE-142363-MS-P, Presented at the SPE Middle East Oil and Gas Show and Conference, Manama, Bahrain, Sep. 2011, 9 pages.

(Continued)

*Primary Examiner* — Kristyn A Hall
(74) *Attorney, Agent, or Firm* — Fish & Richardson P.C.

(57) ABSTRACT

A system and methods for petro-steering methodologies are provided. An exemplary method obtains rock fabric data, and integrate rock fabric data with dynamic productivity data to identify patterns between the rock fabric data and dynamic productivity data. Gas rates and steering values are predicted across UBCT wells based on the patterns.

18 Claims, 16 Drawing Sheets

(56) References Cited

U.S. PATENT DOCUMENTS

| | | |
|---|---|---|
| 8,463,549 B1 | 6/2013 | Selman |
| 8,498,848 B2 | 7/2013 | Habashy et al. |
| 9,835,009 B2 | 12/2017 | Hess et al. |
| 10,260,319 B2 | 4/2019 | Sarduy et al. |
| 10,487,587 B2 | 11/2019 | Cummins |
| 10,570,707 B2 | 2/2020 | Revheim |
| 10,890,066 B1 | 1/2021 | Ibrahim et al. |
| 10,968,730 B2 | 4/2021 | Wang et al. |
| 11,261,720 B2 | 3/2022 | Aziz et al. |
| 11,352,879 B2 | 6/2022 | Li et al. |
| 2006/0090934 A1 | 5/2006 | Williams et al. |
| 2006/0161406 A1 | 7/2006 | Kelfoun et al. |
| 2006/0241867 A1 | 10/2006 | Kuchuk et al. |
| 2007/0016389 A1 | 1/2007 | Ozgen |
| 2008/0172272 A1 | 7/2008 | Back et al. |
| 2008/0289877 A1 | 11/2008 | Nikolakis-Mouchas |
| 2009/0119082 A1 | 5/2009 | Fitzpatrick et al. |
| 2010/0059220 A1 | 3/2010 | Wilberg et al. |
| 2011/0098931 A1 | 4/2011 | Kosmala et al. |
| 2011/0161133 A1 | 6/2011 | Staveley |
| 2012/0048618 A1 | 3/2012 | Zamanian et al. |
| 2013/0124171 A1 | 5/2013 | Schuette et al. |
| 2013/0140088 A1 | 6/2013 | Williams et al. |
| 2013/0144531 A1 | 6/2013 | Johnston |
| 2013/0311096 A1 | 11/2013 | Greer et al. |
| 2014/0124265 A1* | 5/2014 | Al-Yami .................. E21B 44/00 175/24 |
| 2014/0209383 A1 | 7/2014 | Vuyk |
| 2015/0012219 A1 | 1/2015 | Selman |
| 2015/0060054 A1 | 3/2015 | Bordoloi et al. |
| 2015/0168286 A1 | 6/2015 | Mikhailov et al. |
| 2015/0218888 A1 | 8/2015 | Schonberger et al. |
| 2015/0240616 A1 | 8/2015 | Woodward et al. |
| 2016/0169856 A1 | 6/2016 | Sung et al. |
| 2017/0096881 A1 | 4/2017 | Dusterhoft et al. |
| 2017/0167254 A1 | 6/2017 | Fotland |
| 2017/0205531 A1 | 7/2017 | Berard et al. |
| 2017/0335665 A1 | 11/2017 | Saleri et al. |
| 2018/0202264 A1 | 7/2018 | Sarduy |
| 2018/0238148 A1 | 8/2018 | Canady et al. |
| 2018/0266245 A1 | 9/2018 | Gillan |
| 2018/0334896 A1 | 11/2018 | Samuel et al. |
| 2019/0114352 A1 | 4/2019 | Sung |
| 2020/0071602 A1* | 3/2020 | Dhawan ................ C04B 24/123 |
| 2020/0157887 A1* | 5/2020 | Alonso .................. E21B 43/30 |
| 2020/0370409 A1* | 11/2020 | Yu ........................... E21B 47/12 |
| 2021/0026030 A1 | 1/2021 | Dixon et al. |
| 2021/0348493 A1 | 11/2021 | Aziz et al. |
| 2021/0357777 A1 | 11/2021 | Sierra et al. |
| 2022/0389798 A1* | 12/2022 | Liu ......................... E21B 44/00 |

OTHER PUBLICATIONS

Blumbaugh, "Cleveland Formation—Recent Results and Lessons Learned During Horizontal Re-development of a Mature Field," SPE-142790-MS-P, Presented at the SPE Middle East Unconventional Gas Conference and Exhibition, Muscat, Oman, Jan. 31-Feb. 2, 2011, 9 pages.

Bybee, "Coiled-Tubing Underbalanced Drilling in the Lisburne Field, Alaska," SPE-0608-0079-JPT, Journal of Petroleum Technology, Jun. 2008, 60(06): 79-82, 3 pages.

Guizada et al., "Application of Underbalanced Coiled Tubing Drilling Technology to Enhance Gas Production in Deep Carbonate Reservoirs," SPE-192786-MS, Presented at the Abu Dhabi International Petroleum Exhibition & Conference, Abu Dhabi, UAE, Nov. 12-15, 2018, 8 pages.

Johnson et al., "Coiled-Tubing Underbalanced Drilling Applications in the Lisburne Field, Alaska," IADC/SPE 108337, Presented at the IADC/SPE Managed Pressure Drilling and Underbalanced Operations Conference and Exhibition, Galveston, Texas, Mar. 28-29, 2007, 11 pages.

Kanfar et al., "Real-time integrated petrophysics: geosteering in challenging geology and fluid systems," SPE Saudi Arabia Section Young Professionals Technical Symposium, Mar. 2012, 10 pages.

Kavanagh et al., "Underbalanced Coiled Tubing Drilling Practices in a Deep, Low-Pressure Gas Reservoir," IPTC-10308-MS, Presented at the International Petroleum Technology Conference, Doha, Qatar, Nov. 21-23, 2005, 9 pages.

Leising et al., "Underbalanced Drilling With Coiled Tubing And Well Productivity," SPE-28870-MS, Presented at the SPE European Petroleum Conference, London, UK, Oct. 25-27, 1994, 16 pages.

Pruitt et al., "Underbalanced Coiled Tubing Drilling Update on a Successful Campaign," SPE-92513-MS, Presented at the SPE/IADC Drilling Conference, Amsterdam, The Netherlands, Feb. 23-25, 2005, 8 pages.

Silva et al., "A Process Delivery Template for an Underbalanced Coiled Tubing Drilling Project from Concept to Execution," SPE-107244-MS, Presented at the SPE/ICoTA Coiled Tubing and Well Intervention Conference and Exhibition, The Woodlands, Texas, Mar. 20-21, 2007, 10 pages.

PCT International Search Report and Written Opinion in International Appln. No. PCT/US2021/031721, dated Aug. 31, 2021, 16 pages.

PCT International Search Report and Written Opinion in International Appln. No. PCT/US2021/031932, dated Sep. 1, 2021, 15 pages.

* cited by examiner

100A

100C

If BHP ↓ ⟶ $\Delta P$ ↑ ⟶ Q ↑ ⟶ PI is the same

If Q ↑ ⟶ PI ↑ (when $\Delta P$ is the same) - new gas

If BHP ↑ ⟶ $\Delta P$ ↓ ⟶ Q ↑ ⟶ PI ↑ - new gas (WHP will increase as well)

PETRO-STEERING METHODOLOGIES DURING UNDER BALANCED COILED TUBING (UBTC) DRILLING OPERATIONS

TECHNICAL FIELD

This disclosure generally relates to hydrocarbon exploitation involving, for example, heterogeneous reservoirs.

BACKGROUND

In exploiting hydrocarbon in heterogeneous reservoirs, underbalanced coiled tubing drilling (UBCTD) enables a cost effective solution to increase and sustain production. Generally, rock properties vary with location in heterogeneous reservoirs. Rate of penetration (ROP) and instantaneous productivity index (PI) information is used as input to a proxy for drilling across good reservoir quality. Relying solely on an ROP and PI proxy results in an increased uncertainty on lateral contribution and gas gain as outputs are not linked with operational changes and geological description.

SUMMARY

An embodiment described herein provides a computer-implemented method for petro-steering. In embodiments, rock fabric data is obtained. The rock fabric data is integrated with dynamic productivity data to identify patterns between the rock fabric data and dynamic productivity data. Gas rates are predicted in an underbalanced coiled tubing drilling wells based on the patterns.

An embodiment described herein provides a system for petro-steering. In embodiments, the system includes one or more memory modules and one or more hardware processors communicably coupled to the one or more memory modules. The one or more hardware processors are configured to execute instructions stored on the one or more memory models to perform operations comprising obtaining rock fabric data. The operations integrate rock fabric data with dynamic productivity data to identify patterns between the rock fabric data and dynamic productivity data. The operations predict gas rates in an underbalanced coiled tubing drilling wells based on the patterns.

An embodiment described herein provides an apparatus for petro-steering. In embodiments, the apparatus includes non-transitory, computer readable, storage medium that stores instructions that, when executed by at least one processor, cause the at least one processor to perform operations comprising obtaining rock fabric data. The operations integrate rock fabric data with dynamic productivity data to identify patterns between the rock fabric data and dynamic productivity data. The operations predict gas rates in an underbalanced coiled tubing drilling wells based on the patterns.

BRIEF DESCRIPTION OF DRAWINGS

FIG. 2 illustrates gas rate and gas gain logic used for benchmarking variable selection.

DETAILED DESCRIPTION

Figure 1A:
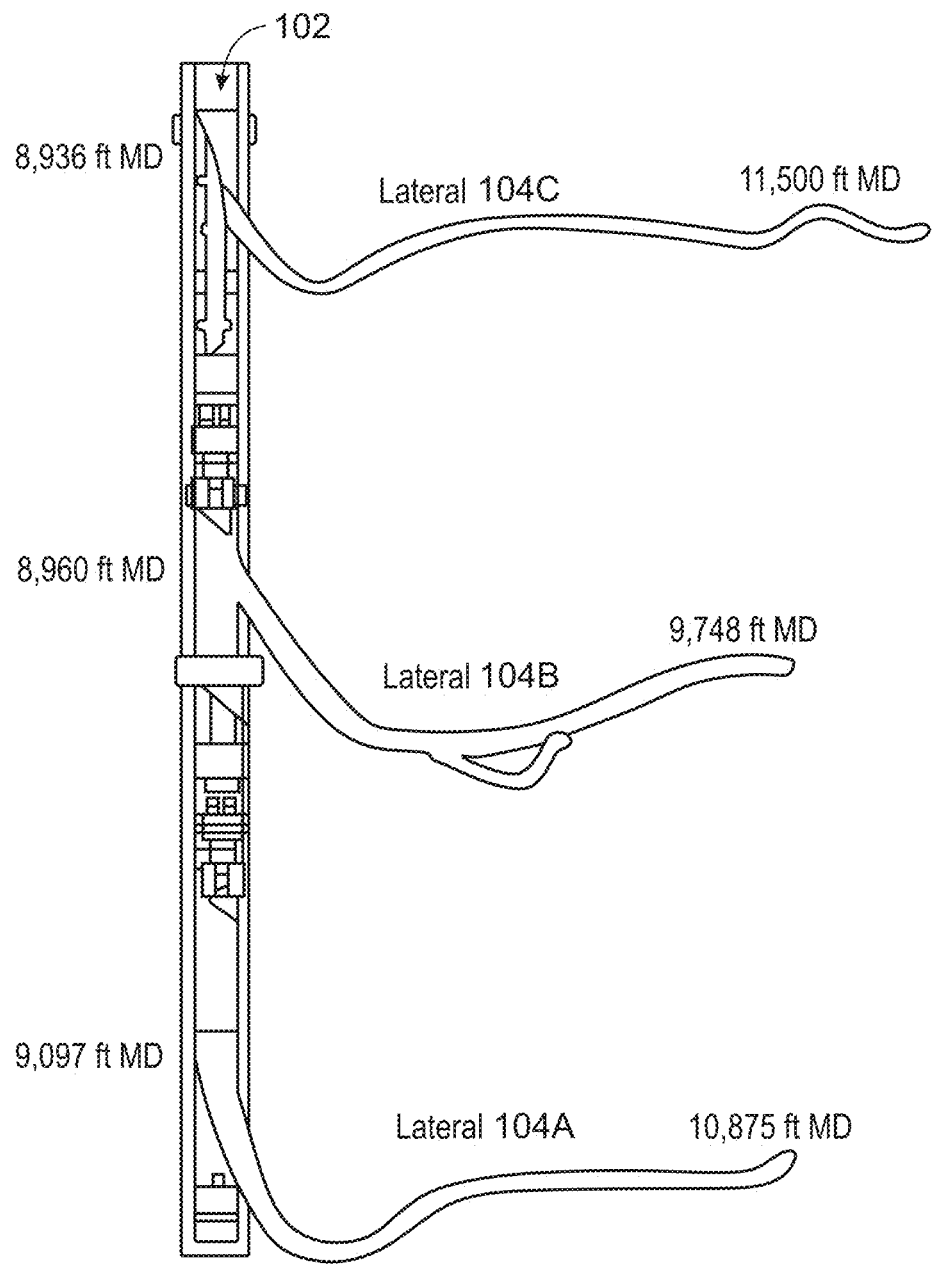
FIG. 1A is an illustration of a well with surface pressure readings.

Generally, heterogeneous reservoirs have mineralogy, organic content, natural fractures, and other properties that vary from place to place. This heterogeneity makes it critical to drill laterals across the best reservoir developments to maximize production. During underbalanced coiled tubing drilling (UBCTD) operations, reservoir engineers receive large amounts of data from different sources such as drilling parameters, well-testing data, bio-steering data, lithological cutting description, and geological inputs. This type of information can be provided by different disciplines using different formats and structures. The variation of formats and structures can make decision-making inefficient as engineers are unable to process and analyze all data generated during drilling operations. As a result, engineers may rely solely on rate of penetration (ROP) and instantaneous productivity index (PI) information as input to a proxy for drilling across good reservoir quality.

Generally, Under Balanced Coiled Tubing Drilling (UBCTD) technology involves drilling a well with fluid pressure lower than the reservoir pressure. Due to the underbalanced condition imposed in the wellbore, the well is allowed to flow naturally during drilling, while its productivity is measured in terms of gas rates and pressures. In embodiments, improved productivity and production sustainability in UBCTD wells is enabled by maximizing the effective reservoir contact in the drilled laterals.

In some cases, barren reservoirs lack good biostratigraphic control. Such barren reservoirs are common in Paleozoic aged hydrocarbon bearing sandstones in, for example, eastern Saudi Arabia. Other biostratigraphically barren successions are found globally. These barren reservoirs are generally devoid of age diagnostic microfossils and palynomorphs, meaning that biostratigraphy cannot be utilized to identify particular stratigraphic beds, including reservoirs. As a result, biostratigraphy techniques cannot be utilized to navigate laterals (e.g., steer) across barren hydrocarbon bearing formations due to the absence of palynomorphs or microfossils. Deployment of UBCTD technology in this type of reservoir generally yields low productivity wells.

Embodiments described herein enable petro-steering methodologies during under balanced coiled tubing (UBTC) drilling operations. In examples, a petro-steering methodology is described that identifies the most productive layers of a hydrocarbon bearing sandstone reservoir in near-real time while drilling UBCTD laterals. In embodiments, near-real time refers to the time it takes for the samples to reach a laboratory (e.g., a laboratory at or near the wellsite) after being drilled and subjected to analysis, including time spent on sample preparation and analysis before the results are available for interpretation. Rock fabric data is integrated with dynamic productivity data to support geosteering of UBCTD laterals in sandstone reservoirs. Generally, rock fabric data describes the mineralogy and geochemistry of the sample. Rock fabric data includes, for example, petrography and geochemical analysis using X-Ray Diffraction (XRD) and X-Ray Fluorescence (XRF). In embodiments, productivity data refers to recorded gas rates and bottom-hole drawdown pressures ($\Delta P$) which are measured during drilling. Productivity Index (PI) is calculated by dividing the gas rate with the $\Delta P$.

For ease of description, the present techniques are described using an exemplary reservoir with three gas wells and twelve UBCTD laterals. However, the present techniques are applicable to a reservoir with any number of gas wells and any number of laterals. In the exemplary reservoir described herein, drilling cuttings are collected regularly every 30 feet (ft) for analysis. Generally, tests applied to the drilling cuttings includes petrography, XRD, and XRF tests on more than 200 drill cuttings.

Referring to FIG. 1A, an example drilling operation 100A is presented to illustrate a lateral configuration for UBCTD according to an implementation of the present disclosure. A wellbore 102 refers to a vertical well. Wellbore 102 may correspond to a motherbore. Drilling operations can include sidetracking one or more laterals from the motherbore to explore reservoir in the horizontal direction. As illustrated, lateral 104A refers to a first window at 9,097 ft measured depth (MD) as a first side track. The lateral 104A reaches a measured depth (MD) of 10,875 ft. Lateral 104B refers to a second window at 8,960 ft measured depth (MD) as a second side track. The lateral 104B reaches a measured depth (MD) of 9,748 ft. Lateral 104C refers to a third window at 8,936 ft measured depth (MD) as a third side track. The lateral 104C reaches a measured depth (MD) of 11,500 ft.

In examples, drilling cuttings were obtained during drilling operation at a wellbore such as wellbore 102. For example, during drilling operations cutting samples are collected, labeled and transported to laboratory facilities where they were analyzed. Three different testing techniques are used to generate rock fabric data: Petrography, X-Ray diffraction (XRD) and X-Ray Fluorescence (XRF). Generally, petrography provides information on the minerals present in individual samples and the character of authigenic minerals and textual components. XRD determines the presence and quantities of specific minerals, and XRF acquires inorganic geochemical data for up to forty elements in the range Na—U in the periodic table.

To use machine learning to identify the elements, ratios, and minerals (data acquired by XRF and XRD) that are most suitable to predict gas flow. In examples, more than two hundred cuttings samples were subjected to petrographic, XRD and XRF analysis. The results were reviewed by subject matter experts (SME) to check data quality prior to interpretation. Over 300 different geochemical parameters, including both individual elements generated by XRF and elemental ratios were examined. For example, the individual elements and elemental ratios include a Silicone Oxide/Aluminum Oxide (Si/Al) ratio, Potassium Oxide (K2O), Potassium (K), Uranium (U) and a Zirconium/Aluminum Oxide (Zr/Al) ratio as illustrated in the plot 100B of FIG. 1B.

In the examples described herein, individual mineral profiles were plotted for each well of the three wells. In particular, cutting samples were processed and analyzed by XRD, in the form of whole rock analysis to identify minerals. For example, mineralogical analysis is executed on randomly oriented powders using a powder X-Ray Diffractometer with Cuka radiation (40 kV, 40 mA), in the 3°-100° (2θ) interval with a step size of 0.02° increment. The XRD patterns are interpreted with a classifier or using cluster analysis to obtain profiles of individual minerals as illustrated in the plot 100C of FIG. 1C. In examples, ditch cuttings were subjected to petrographic analysis in order to determine the percentages of the most abundant minerals and lithic fragments to obtain rock fabric data. Additionally, grain size, sorting, roundness, and occurrence of quartz overgrowths were recorded as rock fabric data.

Figure 1B:
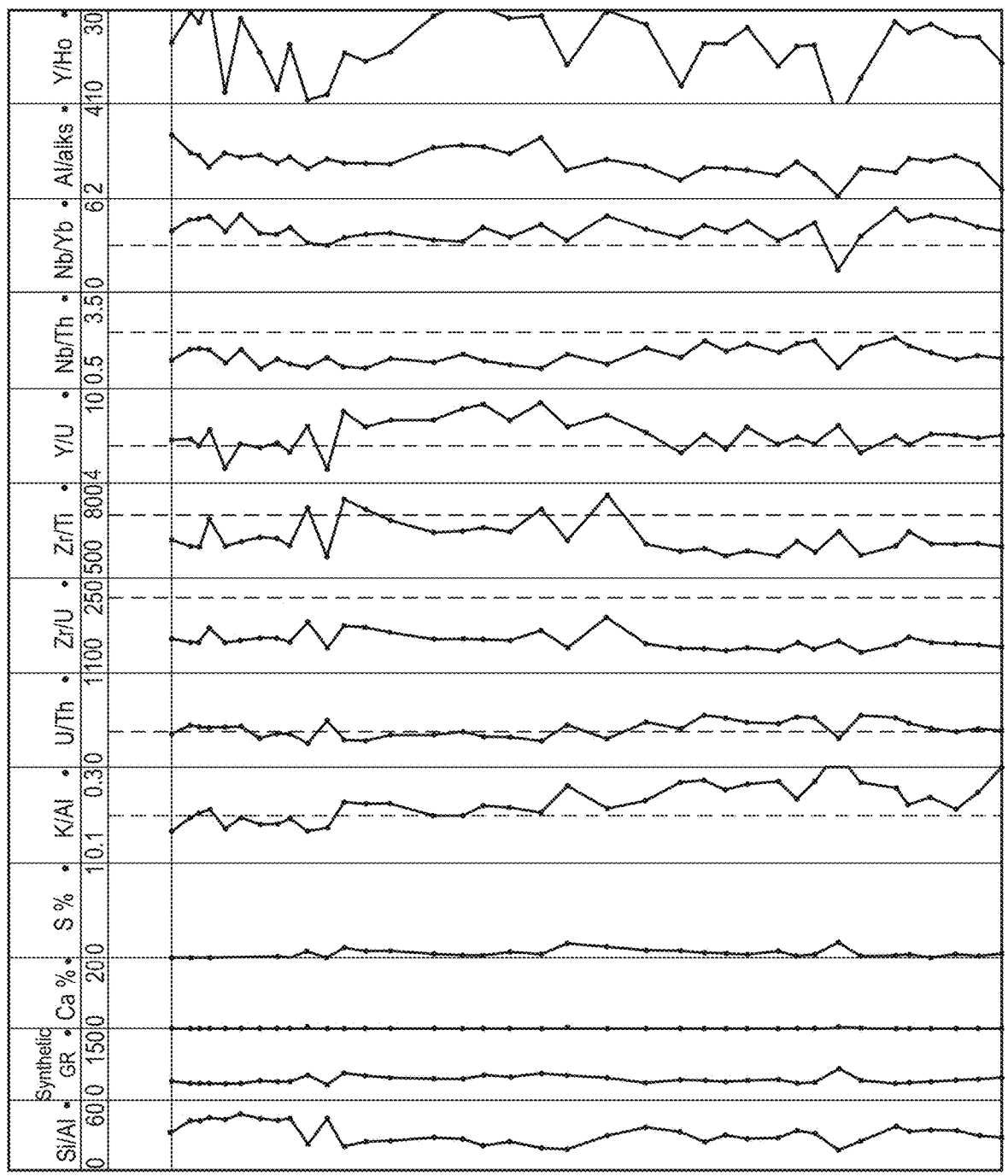
FIG. 1B is a plot of X-Ray Fluorescence data.
Figure 1C:
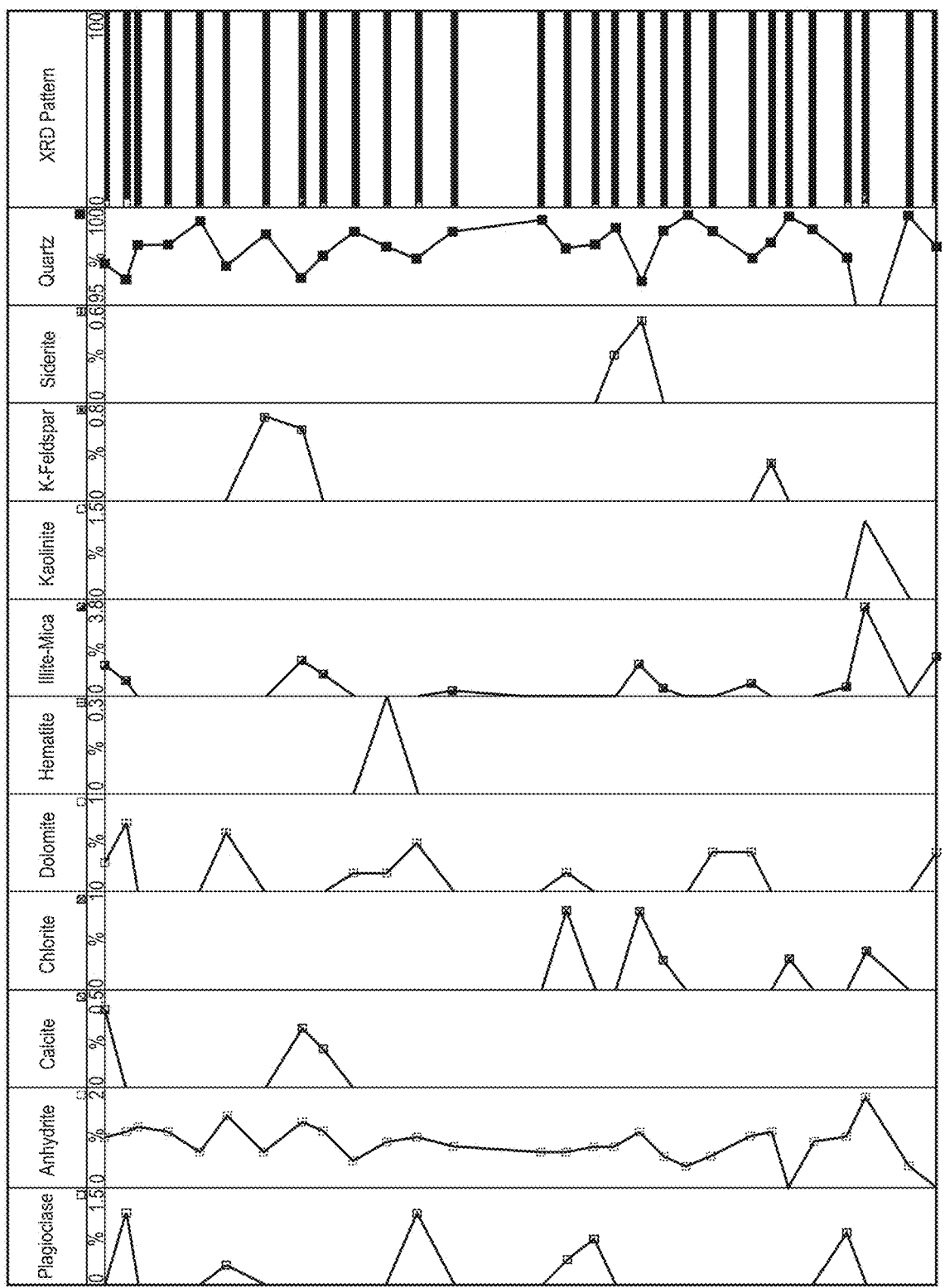
FIG. 1C is a plot of X-ray Diffraction data.

Results from the petrography, XRD, and XRF are integrated with UBCTD productivity data and drilling data to identify patterns between petrography, geochemistry, mineralogy, lithology description and well dynamic performance to be used as proxy for UBCTD lateral placement across "sweet spots" of a hydrocarbon bearing sandstone reservoirs. In some cases, patterns are associations between geochemistry, mineralogy and gas flow rates. The most useful elements and elemental ratios are identified in order to predict such rates. Generally, to integrate of rock fabric data with dynamic productivity data, the dynamic productivity data and rock fabric data (i.e. XRF, XRD, petrography) are plotted in profile form in tracks beside each other as well as in the form of crossplots as illustrated in FIG. 1B and FIG. 1C. Generally, the dynamic productivity data includes a gas rate at a surface of the well, surface and bottom-hole pressure measurement, choke size, and an artificial gas lift. The drilling data includes rate of penetration, footage drilled, gamma-ray response, inclination and azimuth. In examples, the laboratory results were integrated with dynamic productivity data and drilling data, and analyzed using advanced statistical tools along with machine learning algorithms to evaluate correlation between more than 150 variables: including lab results from XRF, XRD and petrography. As a result of this analysis, several geochemical proxies were correlated with gas-gain/higher productivity and therefore can be used to identify productive intervals in hydrocarbon bearing sandstones. Accordingly, the present techniques predict gas rates and steering within the most productive parts of a tight gas bearing permo-carboniferous sandstone reservoir. Post-flowback analyses have shown significant improvement in the well deliverability.

In embodiments, the dynamic (i.e. productivity data generated during drilling such as pressures and gas rates) and static data (i.e. geochemical data generated by XRD and mineralogical data acquired by XRD) is cleaned, reviewed and integrated, with a selection of benchmark variables generated. Variables include: instantaneous PI (Equation 1), Cumulative PI (Equation 2) and Normalized PI (Equation 4) and first derivative of Normalised PI (Equation 5). FIG. 2 illustrates gas rate and gas gain logic used for benchmarking variable selection.

$$PI = \frac{Q}{\Delta P} \qquad \text{Equation 1}$$

$$CumPI = \sum_{lat=1}^{Lat=ln} \sum_{F=0}^{n} PI_{lat,F} \qquad \text{Equation 2}$$

$$Cum\ lenght = \sum_{lat=1}^{Lat=ln} \sum_{F=0}^{n} \cdot F_{lat} \qquad \text{Equation 3}$$

$$NormPI = \frac{CumPI}{Cumlength} \qquad \text{Equation 4}$$

$$\text{Norm\_PI}' = f'(Norm\ PI) \qquad \text{Equation 5}$$

Where:
PI=Productivity index
Q=Gas Rate
ΔP=Differential Pressure (Reservoir Pressure—Measured Bottom-hole Pressure)
Cum PI=Summation of PI across all laterals
lat=number of lateral
F=total footage
Cum length=summation of all footage drilled across all laterals
Norm PI=normalized Productivity index
Norm Pi' (NPIFD)=first derivative of Normalized PI between $PI_{n-1}$ and $PI_n$ FIG. 2 illustrates gas rate and gas gain logic used for benchmarking variable selection. Generally, a gas gain results from an increase in gas rates. In embodiments, advanced data analytics techniques enable an understanding of data relationships capitalizing on advanced statistical methodologies (i.e. Exploratory Data Analysis) and AI techniques (i.e. machine learning) to benchmark and predict reference variables (i.e. gas gain).

In the example of FIG. 2, a decrease in bottom hole pressure (BHP) correlates to in an increase in differential reservoir pressure, which correlates to an increase in gas rate. The corresponding productivity index remains the same. In the example of FIG. 2, an increase in gas rate correlates to an increase in the productivity index when the differential reservoir pressure is the same. Additionally, in the example of FIG. 2, an increase in bottom hole pressure correlates to a decrease in differential reservoir pressure, which correlates to an increase in gas rate and an increase in the productivity index. The wellhead pressure will increase as well.

Figure 3:
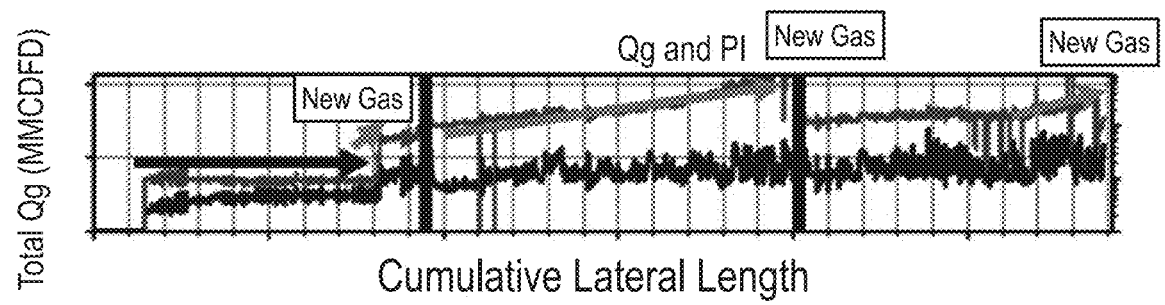
FIG. 3 is an illustration of cumulative lateral length.
Figure 3:
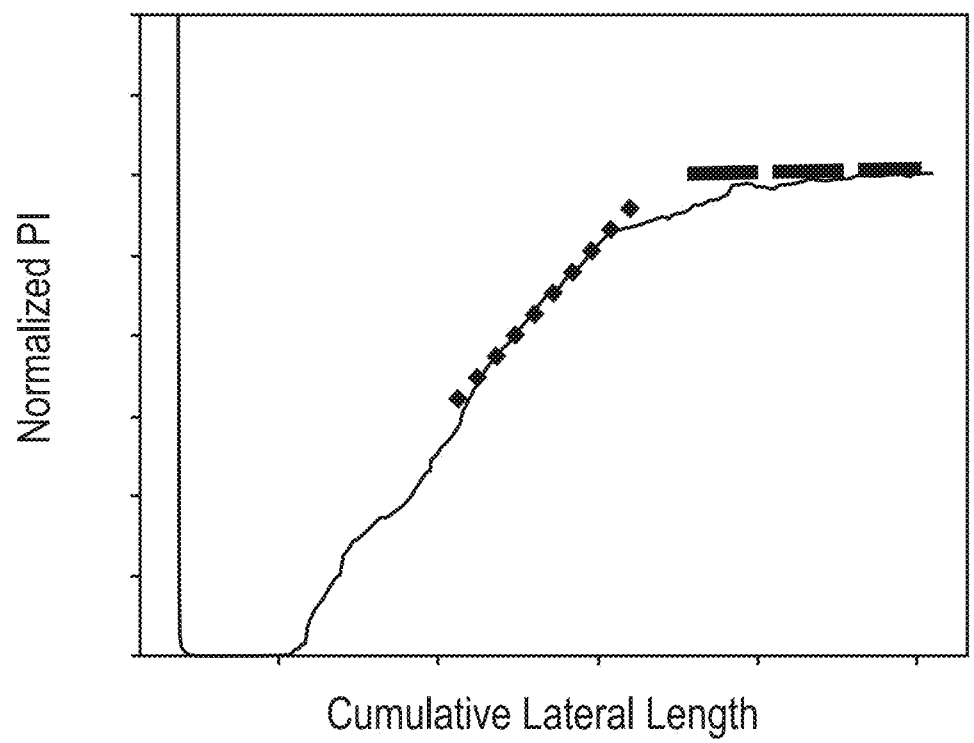

Multi-variable analysis is executed to identify the best parameter to benchmark well performance with laboratory results. The analysis shows that the best variable to be used for dynamic-laboratory correlation is the Normalized PI's first derivative. As shown in FIG. 3, when a lateral well penetrates productive intervals, the first derivative of normalized PI increases. In examples, a productive interval is a "sweet spot" for drilling. On the other hand, when a poor quality reservoir is drilled, the normalized PI first derivative decreases towards zero.

Exploratory Data Analysis (EDA) is implemented to determine relationships between laboratory tests (Petrography, XRD and XRF) and Normalized PI's first derivative. In order to establish whether differences or associations exist between datasets, inferential statistical analysis is utilized. Each lab output result is compared with a benchmark variable to establish whether the drilled interval contributed to the production. Samples are split into two groups depending on dynamic performance at the collected sample depth, i.e. if the slope of NPIFD is close to zero at sample depth, the sample was assigned to No_Gas_Gain group (plotted as black X's in FIGS. 4-6), otherwise the sample was assigned to Gas_Gain group (plotted as grey, filled O's in FIGS. 4-6)

Figure 4:
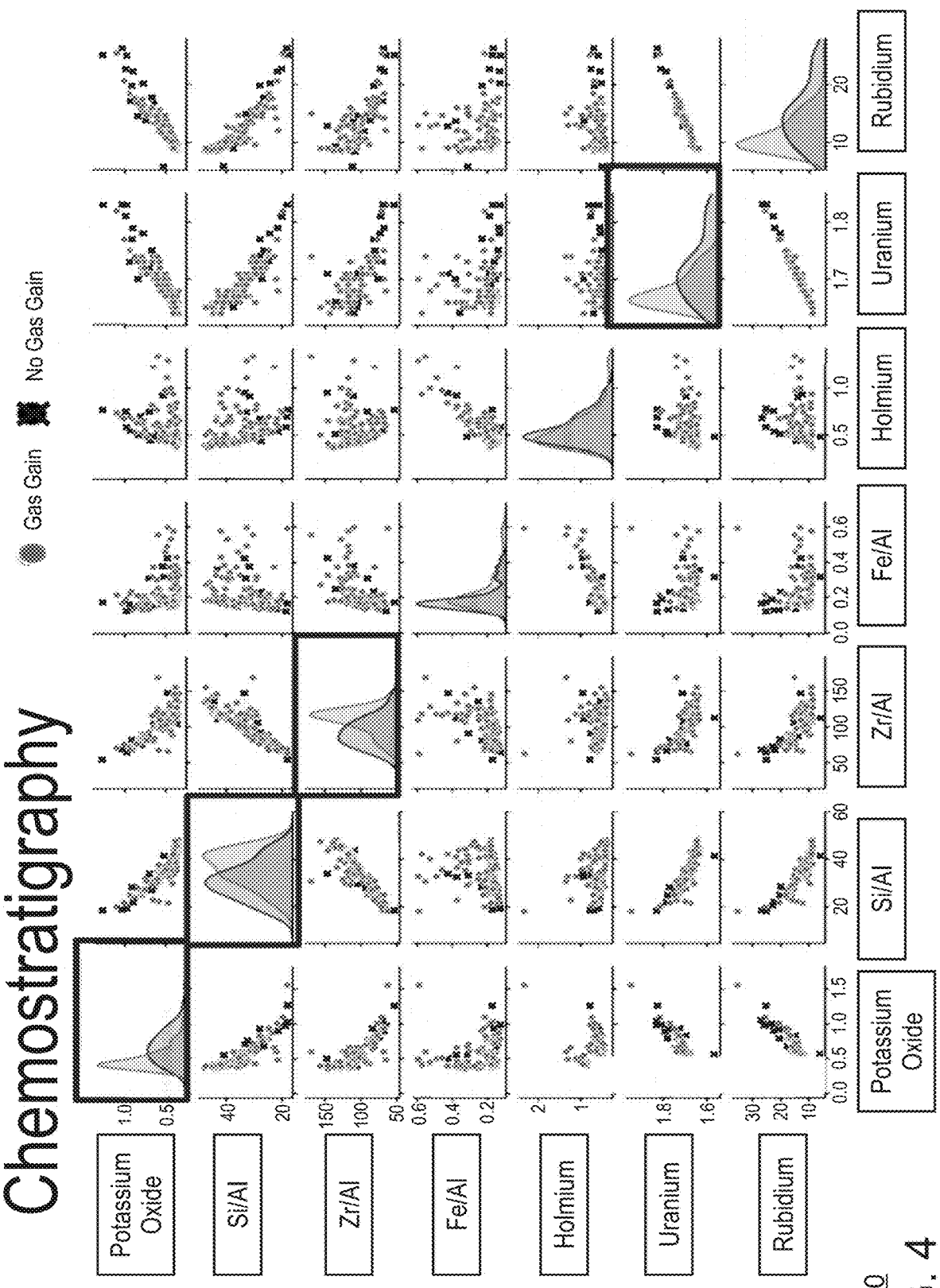
FIG. 4 is an illustration of summarized inferential statistical analysis of XRF results.
Figure 5:
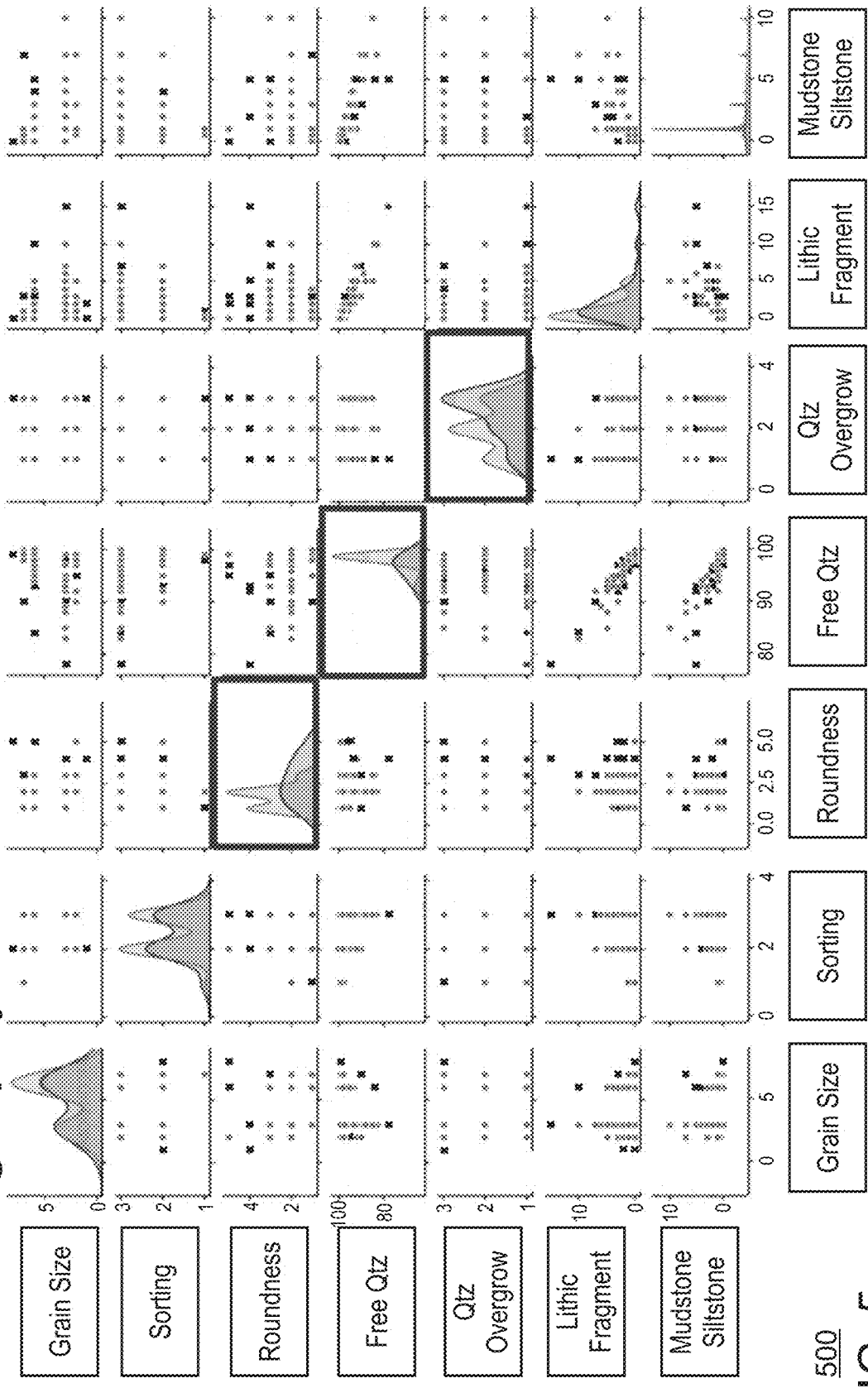
FIG. 5 is an illustration of exploratory data analysis of petrography results.
Figure 6:
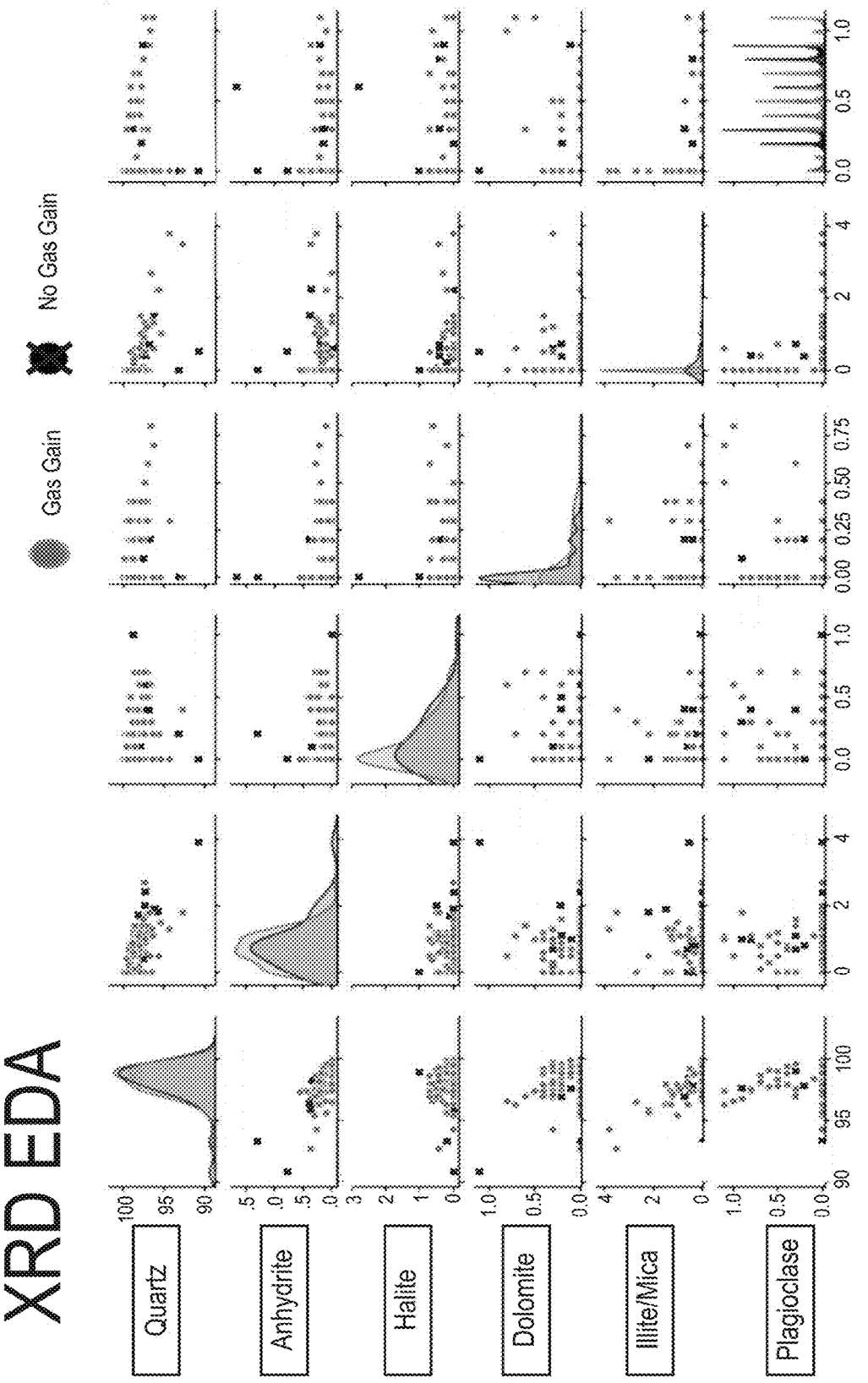
FIG. 6 is an illustration of exploratory data analysis of XRD results.

The paired plots of FIG. 4 illustrate a summary of inferential statistical analysis of XRF results (e.g., rock fabric data). The plots 400 visualize how variables correlate/differ among themselves. The diagonal plots 402 show dataset population distribution between the two families (gas-gain and no-gas-gain). In general, if both population datasets overlap, there is association between properties. On the other hand, if there is a separation, an inference is made that the variable can be used a predictor to determine the gas gain. Measurements with a high correlation are highlighted with a black box. For example, the Si/Al gas-gain median is different from no-gas-gain population meaning that this ratio can be used as a parameter to identify favorable productivity intervals. Similar behavior was observed for K, Zr/Al and U. Some of the petrography measurements in FIG. 5 are subjective values such roundness, sorting, gain size and quartz overgrowths, making their identification more challenging. Overall, petrography results of FIG. 5 show a moderate correlation with properties such as grain roundness, free quartz content and quartz overgrowth with dynamic data. On the other hand, XRD in FIG. 6 did not show any correlation to the gas-gain.

Figure 7:
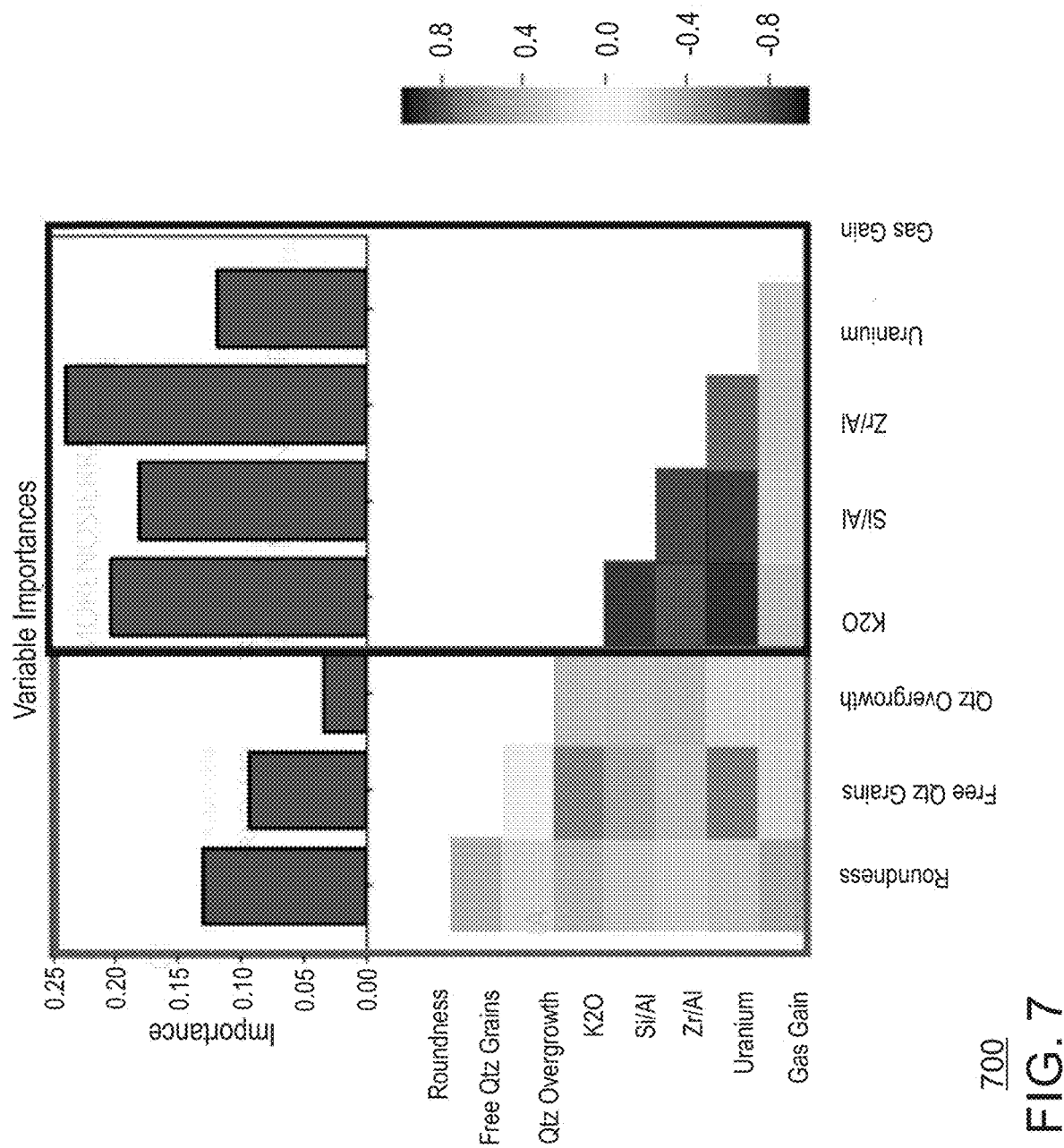
FIG. 7 is an illustration of variable reduction.

In examples, more than 300 variables were reported from all tests. In order to process and select the most important variables for identification of productive intervals, a machine-learning (ML) model is trained. The objective of training the machine learning model is to predict gas gain (Normalized PI first derivative), based on rock fabric data. In embodiments, the machine learning model reduces the number of variables to be used as proxies to identify high productive layers. As illustrated in FIG. 7, variable input is reduced from 300 parameters to seven parameters. Those parameters were selected to be validated with dynamic performance from the laterals.

Figure 8:
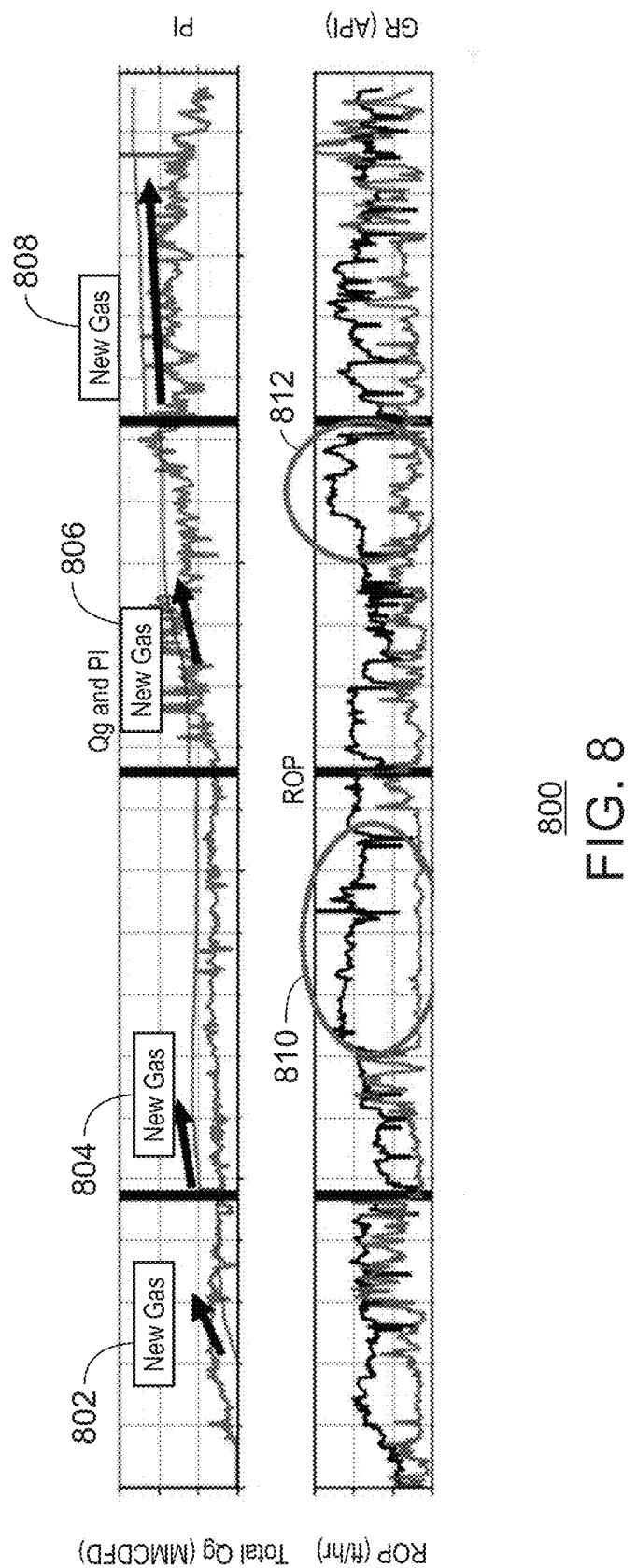
FIG. 8 is an illustration of exemplary visual results to predict gas rates and steering.

FIG. 8 is an illustration of exemplary visual results that predict gas rates and steering values. Traditionally, a high ROP was used as a proxy for soft rock, which implies high porosity/permeability and gas gain. It is highlighted by circles 810 and 812, where high ROP values are reported across no gas gain intervals (no increases on Normalized PI). Potentially there is uncertainty on gas-gain, however, due to operational factors such as overbalance pressure, wellbore stability or sub-hydrostatic reservoir pressure. In the example of FIG. 8, the well did not experience any of those factors.

Figure 9:
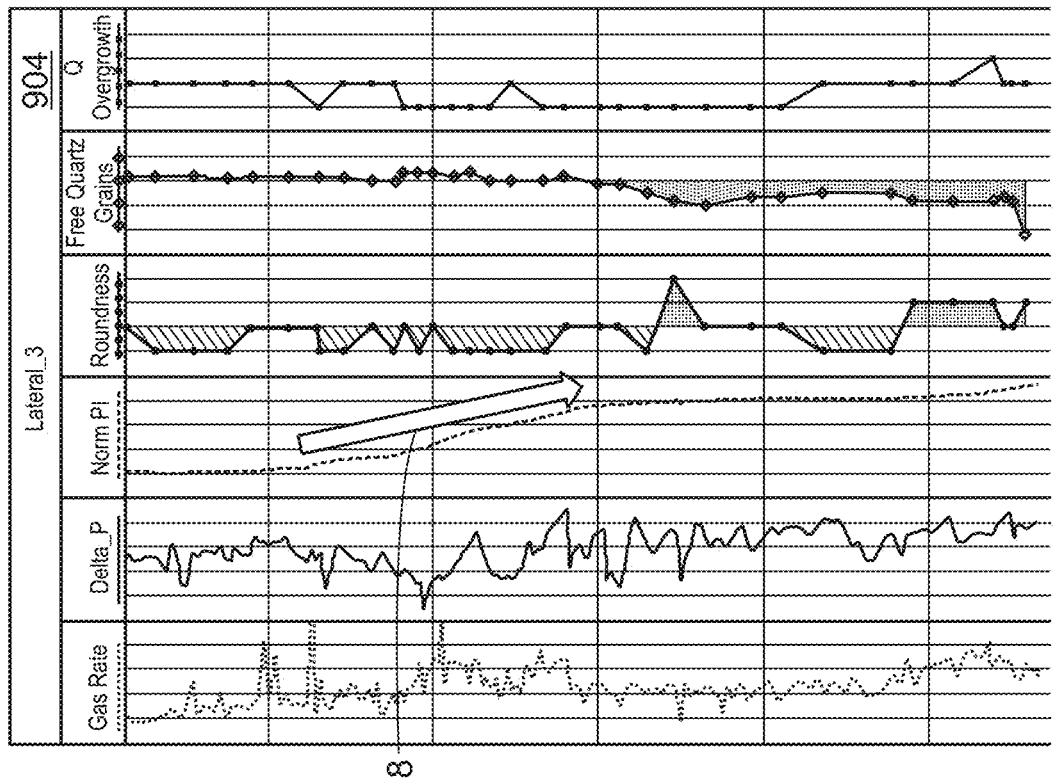
FIG. 9 is an illustration of dynamic productivity data associated with laterals.
Figure 9:
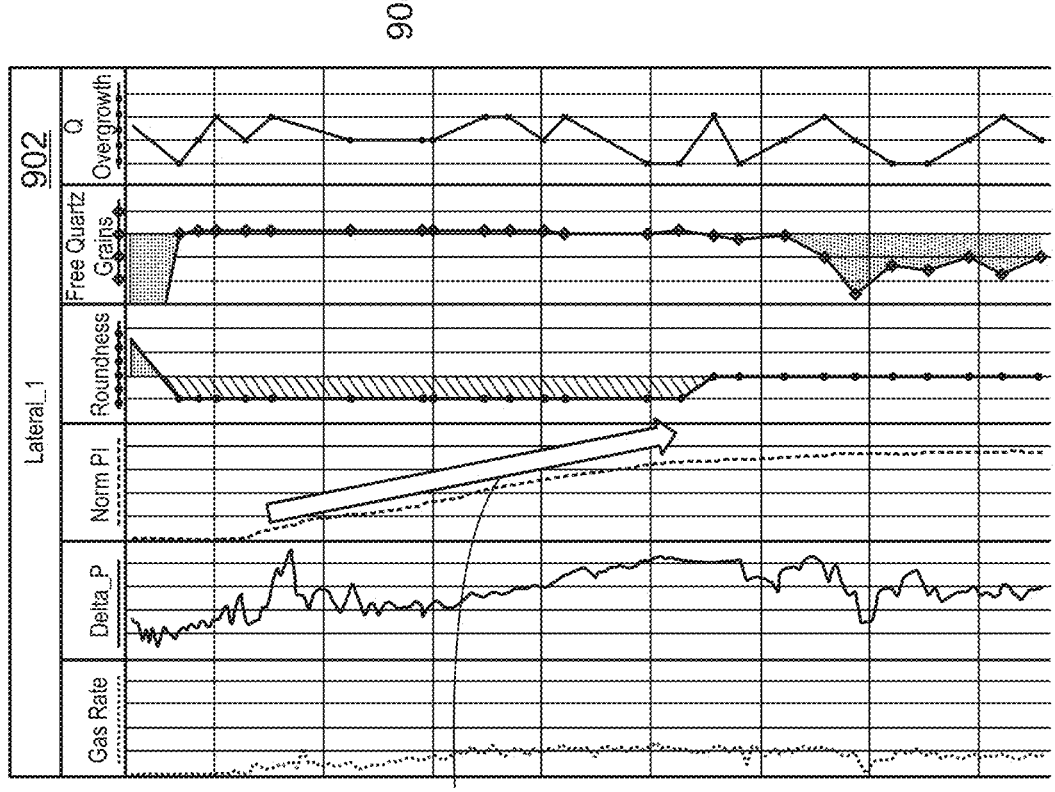

The plots of FIG. 9 compare dynamic productivity data such as Gas Rate, ΔP (Reservoir pressure–flowing borehole pressure), and Norm_PI in tracks 1-3 respectively with most relevant petrography parameters such as roundness, Free Quartz Grains (FQG) and quartz overgrowth in tracks 4-6 respectively. Laterals are from the same exemplary well. Arrows 906 and 908 highlight intervals where high production was encountered. In first lateral 902, a good correlation is observed between high roundness index (diagonal shaded areas 910 and 912) and high free quartz grains (FQG) across the highly productive interval. The trends are not, however, consistent across all laterals as illustrated in the Lateral_3 plot 904. As a result, petrography and XRD parameters were excluded for identifying highly productive zones.

Figure 10:
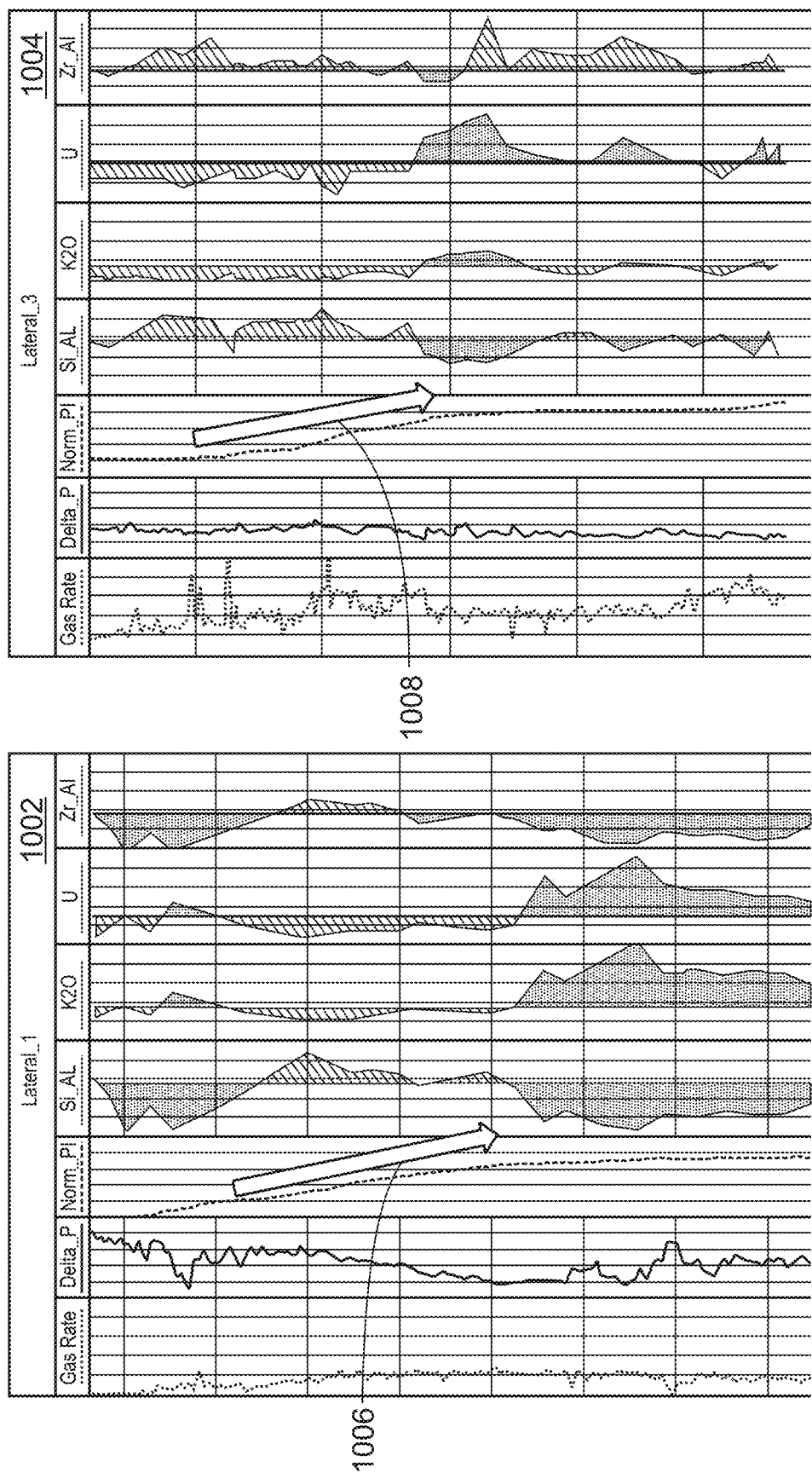
FIG. 10 is an illustration of a comparison of dynamic productivity data with XRF measured elements.

The plots in FIG. 10 compare dynamic productivity data such as gas rate, ΔP (Reservoir pressure–Flowing Borehole pressure, and Norm_PI in tracks 1-3 respectively with the most relevant XRF measured elements/ratios such as Si/Al, K, U and Zr/Al in tracks 4-7 respectively. Laterals 1002 and 1004 are from the same exemplary well. Arrows 1006 and 1008 highlight the penetration of high productive intervals. The following is a brief description of the selected XRF elements.

Silicone Oxide/Aluminum Oxide ratio (Si/Al):Si is mainly present in quartz, Al occurs in clay minerals, thus high Si/Al ratios are an indication of quartz dominated intervals with low clay contents.

Potassium Oxide K2O is an element predominately present in clays such as illite. Through the pilot project, we observed that a small increment on clay content could have a detrimental effect on PI.

Uranium: low values in Uranium are related to low presence of clay material.

Zirconium/Aluminum Oxide ratio (Zr/Al) is related to Al-bearing clay minerals.

Results show that there is an excellent correlation between the high productive intervals (additional gas-gain) and high Si/Al ratios with low clay mineral contents.

Figure 11:
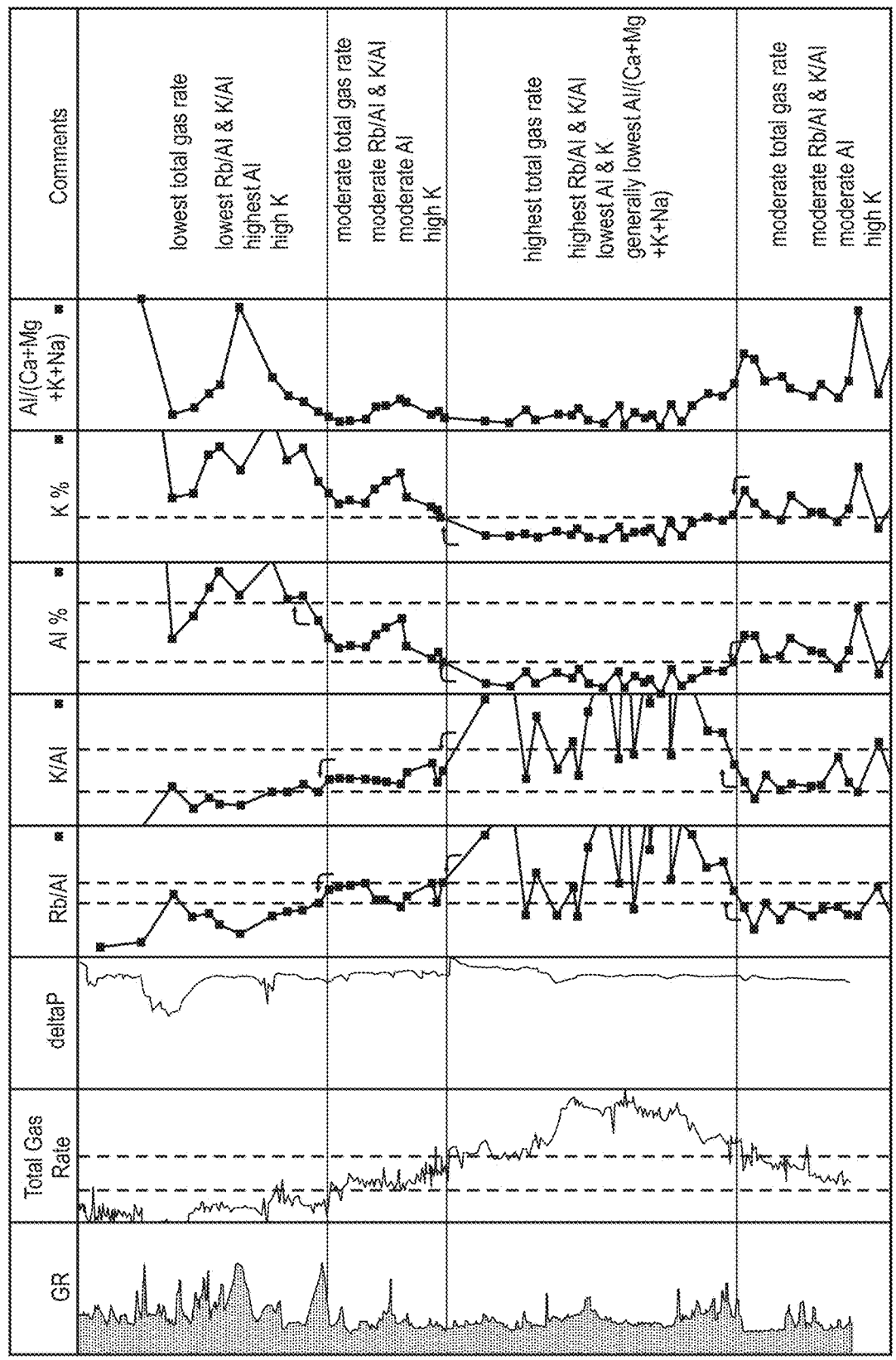
FIG. 11 is an illustration of petro-steering results.
Figure 12:
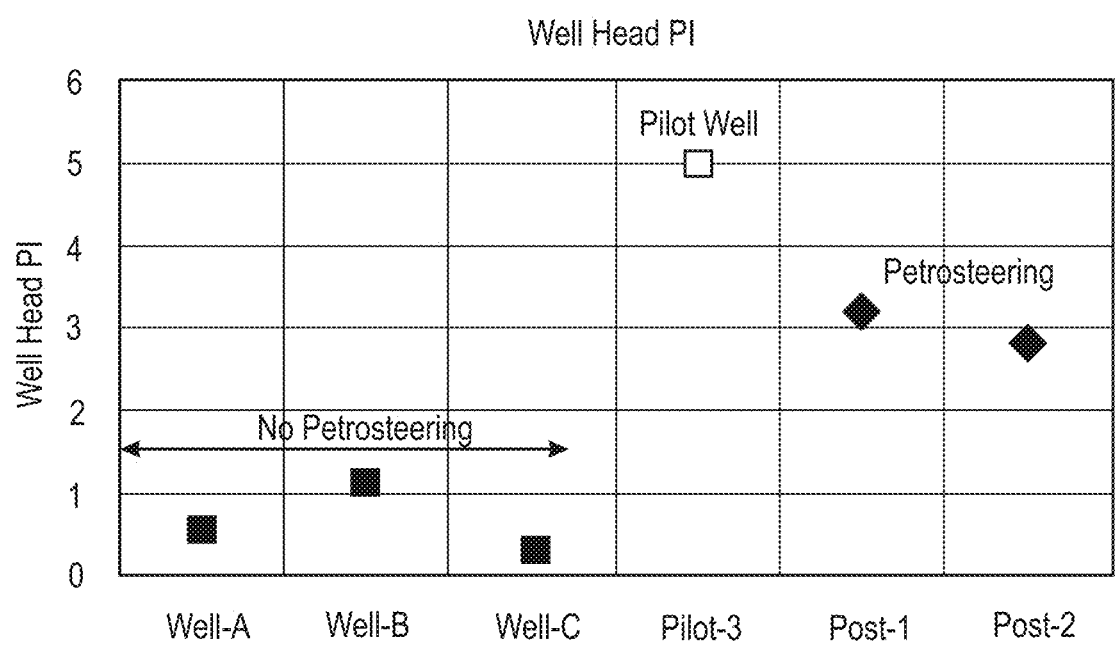
FIG. 12 is a comparison of petro-steering results according to the present techniques and conventional geosteering results.

In the examples described herein, after initial drilling operations, two additional gas wells were drilled across the sandstone formations using petro-steering the results of which are shown in FIG. 11. After deploying petro-steering as described herein, wellhead PI increased by three-fold compare with historical UBCTD wells geosteered with conventional techniques as illustrated in FIG. 12. Accordingly, the present techniques use rock fabric data results measured in near-real time with a combination of dynamic productivity data to identify "sweet spot" intervals. This will improve reservoir contact and consequently well deliverability.

Figure 13:
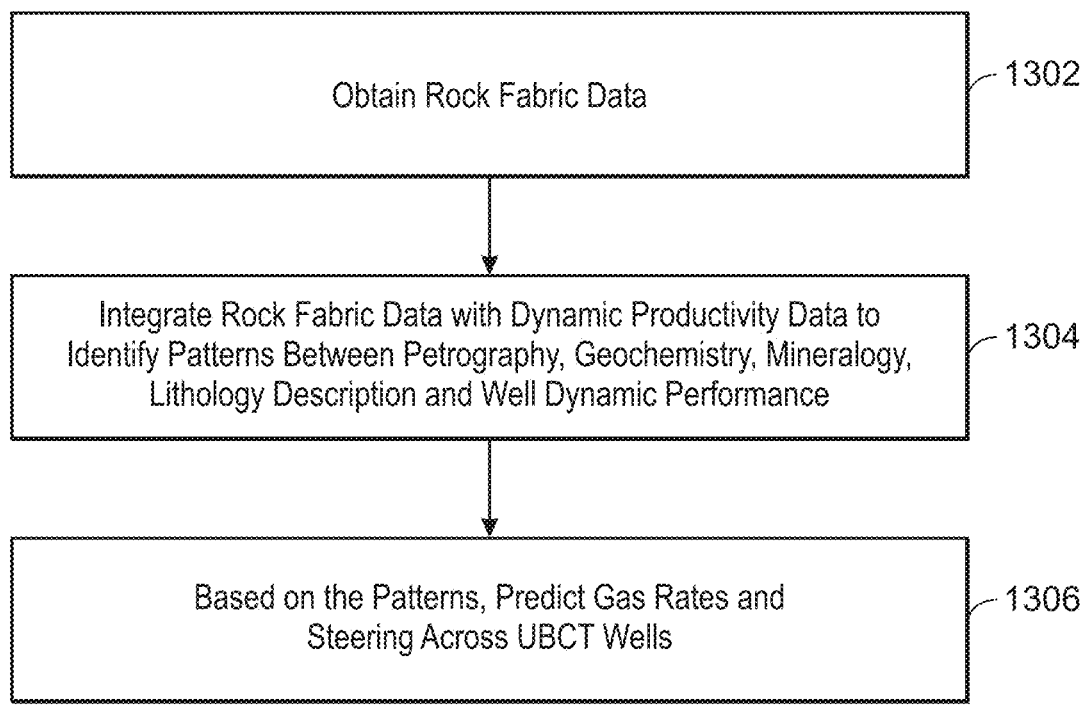
FIG. 13 is a process flow diagram of a process for petro-steering.

FIG. 13 is a process flow diagram of a method for petro-steering as described herein. At block 1302, rock fabric data is obtained. In examples, rock fabric data includes data obtained using petrography, and geochemical analysis using XRD and XFD data. In examples, during drilling operations cutting samples are collected, labeled and transported to laboratory facilities where they are analyzed. At block 1304, rock fabric data is integrated with dynamic productivity data (e.g., UBCTD well testing and drilling data) to identify patterns between petrography, geochemistry, mineralogy, lithology description and well dynamic performance. In embodiments, patterns are identified by comparing gas rates, ΔP and Norm PI with geochemical and mineralogical data. Each rock fabric dataset can be plotted in profile track and in the form of crossplots.

At block 1306, gas rates and steering across UBCTD wells is predicted based on the patterns between petrography, geochemistry, mineralogy, lithology description and well dynamic performance. In particular, the predicted gas rates and steering values are used to guide petro-steering during drilling operations to locations that are predicted to have a high productivity (where productivity is measured in terms of gas rates and pressures). In embodiments, the gas rates and steering values generate UBCTD laterals across "sweet spots" in sandstone reservoirs. Accordingly, the petro-steering workflow as described herein integrates XRF analysis and XRD analysis with dynamic performance in real-time for UBCTD wells across biostratigraphy barren formations. This data integration maximizes reservoir contact and improved decision-making process while drilling UBCTD wells.

Figure 14:
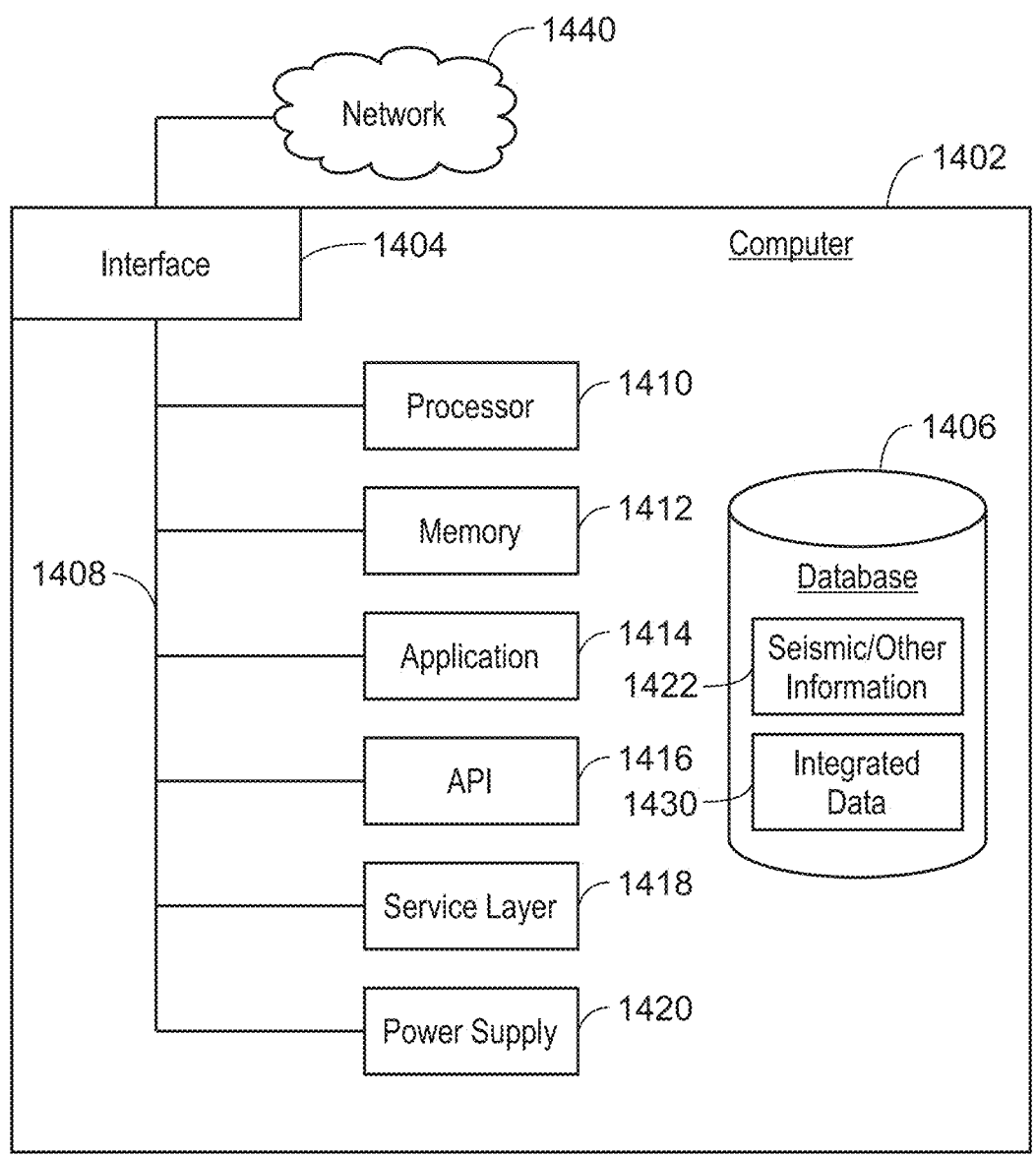
FIG. 14 is a block diagram of an example computer system that enables petro-steering.

FIG. 14 is a block diagram of an example computer system 1400 used to provide computational functionalities associated with described algorithms, methods, functions, processes, flows, and procedures described in the present disclosure for petro-steering methodologies, according to some implementations of the present disclosure.

The illustrated computer 1402 is intended to encompass any computing device such as a server, a desktop computer, a laptop/notebook computer, a wireless data port, a smart phone, a personal data assistant (PDA), a tablet computing device, or one or more processors within these devices, including physical instances, virtual instances, or both. The computer 1402 can include input devices such as keypads, keyboards, and touch screens that can accept user information. Also, the computer 1402 can include output devices that can convey information associated with the operation of the computer 1402. The information can include digital data, visual data, audio information, or a combination of information. The information can be presented in a graphical user interface (UI) (or GUI).

The computer 1402 can serve in a role as a client, a network component, a server, a database, a persistency, or components of a computer system for performing the subject matter described in the present disclosure. The illustrated computer 1402 is communicably coupled with a network 1440. In some implementations, one or more components of the computer 1402 can be configured to operate within different environments, including cloud-computing-based environments, local environments, global environments, and combinations of environments.

Generally, the computer 1402 is an electronic computing device operable to receive, transmit, process, store, and manage data and information associated with the described subject matter. According to some implementations, the computer 1402 can also include, or be communicably coupled with, an application server, an email server, a web server, a caching server, a streaming data server, or a combination of servers.

The computer 1402 can receive requests over network 1440 from a client application (for example, executing on another computer 1402). The computer 1402 can respond to the received requests by processing the received requests using software applications. Requests can also be sent to the computer 1402 from internal users (for example, from a command console), external (or third) parties, automated applications, entities, individuals, systems, and computers.

Each of the components of the computer 1402 can communicate using a system bus 1408. In some implementations, any or all of the components of the computer 1402, including hardware or software components, can interface with each other or the interface 1404 (or a combination of both), over the system bus 1408. Interfaces can use an application programming interface (API) 1416, a service layer 1418, or a combination of the API 1416 and service layer 1418. The API 1416 can include specifications for routines, data structures, and object classes. The API 1416 can be either computer-language independent or dependent. The API 1416 can refer to a complete interface, a single function, or a set of APIs.

The service layer 1418 can provide software services to the computer 1402 and other components (whether illustrated or not) that are communicably coupled to the computer 1402. The functionality of the computer 1402 can be accessible for all service consumers using this service layer. Software services, such as those provided by the service layer 1418, can provide reusable, defined functionalities through a defined interface. For example, the interface can be software written in JAVA, C++, or a language providing data in extensible markup language (XML) format. While illustrated as an integrated component of the computer 1402, in alternative implementations, the API 1416 or the service layer 1418 can be stand-alone components in relation to other components of the computer 1402 and other components communicably coupled to the computer 1402. Moreover, any or all parts of the API 1416 or the service layer 1418 can be implemented as child or sub-modules of another software module, enterprise application, or hardware module without departing from the scope of the present disclosure.

The computer 1402 includes an interface 1404. Although illustrated as a single interface 1404 in FIG. 14, two or more interfaces 1404 can be used according to particular needs, desires, or particular implementations of the computer 1402 and the described functionality. The interface 1404 can be used by the computer 1402 for communicating with other systems that are connected to the network 1440 (whether illustrated or not) in a distributed environment. Generally, the interface 1404 can include, or be implemented using, logic encoded in software or hardware (or a combination of software and hardware) operable to communicate with the network 1440. More specifically, the interface 1404 can include software supporting one or more communication protocols associated with communications. As such, the network 1440 or the interface's hardware can be operable to communicate physical signals within and outside of the illustrated computer 1402.

The computer 1402 includes a processor 1410. Although illustrated as a single processor 1410 in FIG. 14, two or more processors 1405 can be used according to particular needs, desires, or particular implementations of the computer 1402 and the described functionality. Generally, the processor 1410 can execute instructions and can manipulate data to perform the operations of the computer 1402, including operations using algorithms, methods, functions, processes, flows, and procedures as described in the present disclosure.

The computer 1402 also includes a database 1406 that can hold data, including seismic data 1416 and rock fabric data 1430 (e.g. petrographic, XRD and XRF analysis results), for the computer 1402 and other components connected to the network 1440 (whether illustrated or not). For example, database 1406 can be an in-memory, conventional, or a database storing data consistent with the present disclosure. In some implementations, database 1406 can be a combination of two or more different database types (for example, hybrid in-memory and conventional databases) according to particular needs, desires, or particular implementations of the computer 1402 and the described functionality. Although illustrated as a single database 1406 in FIG. 14, two or more databases (of the same, different, or combination of types) can be used according to particular needs, desires, or particular implementations of the computer 1402 and the described functionality. While database 1406 is illustrated as an internal component of the computer 1402, in alternative implementations, database 1406 can be external to the computer 1402.

The computer 1402 also includes a memory 1412 that can hold data for the computer 1402 or a combination of components connected to the network 1440 (whether illustrated or not). Memory 1412 can store any data consistent with the present disclosure. In some implementations, memory 1412 can be a combination of two or more different types of memory (for example, a combination of semiconductor and magnetic storage) according to particular needs, desires, or particular implementations of the computer 1402 and the described functionality. Although illustrated as a single memory 1412 in FIG. 14, two or more memories 1412 (of the same, different, or combination of types) can be used according to particular needs, desires, or particular implementations of the computer 1402 and the described functionality. While memory 1412 is illustrated as an internal component of the computer 1402, in alternative implementations, memory 1412 can be external to the computer 1402.

The application 1414 can be an algorithmic software engine providing functionality according to particular needs, desires, or particular implementations of the computer 1402 and the described functionality. For example, application 1414 can serve as one or more components, modules, or applications. Further, although illustrated as a single application 1414, the application 1414 can be implemented as multiple applications 1414 on the computer 1402. In addition, although illustrated as internal to the computer 1402, in alternative implementations, the application 1414 can be external to the computer 1402.

The computer 1402 can also include a power supply 1420. The power supply 1420 can include a rechargeable or non-rechargeable battery that can be configured to be either user- or non-user-replaceable. In some implementations, the power supply 1420 can include power-conversion and management circuits, including recharging, standby, and power management functionalities. In some implementations, the power-supply 1420 can include a power plug to allow the computer 1402 to be plugged into a wall socket or a power source to, for example, power the computer 1402 or recharge a rechargeable battery.

There can be any number of computers 1402 associated with, or external to, a computer system containing computer 1402, with each computer 1402 communicating over network 1440. Further, the terms "client," "user," and other appropriate terminology can be used interchangeably, as appropriate, without departing from the scope of the present disclosure. Moreover, the present disclosure contemplates that many users can use one computer 1402 and one user can use multiple computers 1402.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Software implementations of the described subject matter can be implemented as one or more computer programs. Each computer program can include one or more modules of computer program instructions encoded on a tangible, non-transitory, computer-readable computer-storage medium for execution by, or to control the operation of, data processing apparatus. Alternatively, or additionally, the program instructions can be encoded in/on an artificially generated propagated signal. The example, the signal can be a machine-generated electrical, optical, or electromagnetic signal that is generated to encode information for transmission to suitable receiver apparatus for execution by a data processing apparatus. The computer-storage medium can be a machine-readable storage device, a machine-readable storage substrate, a random or serial access memory device, or a combination of computer-storage mediums.

The terms "data processing apparatus," "computer," and "electronic computer device" (or equivalent as understood by one of ordinary skill in the art) refer to data processing hardware. For example, a data processing apparatus can encompass all kinds of apparatus, devices, and machines for processing data, including by way of example, a programmable processor, a computer, or multiple processors or computers. The apparatus can also include special purpose logic circuitry including, for example, a central processing unit (CPU), a field programmable gate array (FPGA), or an application specific integrated circuit (ASIC). In some implementations, the data processing apparatus or special purpose logic circuitry (or a combination of the data processing apparatus or special purpose logic circuitry) can be hardware- or software-based (or a combination of both hardware- and software-based). The apparatus can optionally include code that creates an execution environment for computer programs, for example, code that constitutes processor firmware, a protocol stack, a database management system, an operating system, or a combination of execution environments. The present disclosure contemplates the use of data processing apparatuses with or without conventional operating systems, for example, LINUX, UNIX, WINDOWS, MAC OS, ANDROID, or IOS.

A computer program, which can also be referred to or described as a program, software, a software application, a module, a software module, a script, or code, can be written in any form of programming language. Programming languages can include, for example, compiled languages, interpreted languages, declarative languages, or procedural languages. Programs can be deployed in any form, including as stand-alone programs, modules, components, subroutines, or units for use in a computing environment. A computer program can, but need not, correspond to a file in a file system. A program can be stored in a portion of a file that holds other programs or data, for example, one or more scripts stored in a markup language document, in a single file dedicated to the program in question, or in multiple coordinated files storing one or more modules, sub programs, or portions of code. A computer program can be deployed for execution on one computer or on multiple computers that are located, for example, at one site or distributed across multiple sites that are interconnected by a communication network. While portions of the programs illustrated in the various figures may be shown as individual modules that implement the various features and functionality through various objects, methods, or processes, the programs can instead include a number of sub-modules, third-party services, components, and libraries. Conversely, the features and functionality of various components can be combined into single components as appropriate. Thresholds used to make computational determinations can be statically, dynamically, or both statically and dynamically determined.

The methods, processes, or logic flows described in this specification can be performed by one or more programmable computers executing one or more computer programs to perform functions by operating on input data and generating output. The methods, processes, or logic flows can also be performed by, and apparatus can also be implemented as, special purpose logic circuitry, for example, a CPU, an FPGA, or an ASIC.

Computers suitable for the execution of a computer program can be based on one or more of general and special purpose microprocessors and other kinds of CPUs. The elements of a computer are a CPU for performing or executing instructions and one or more memory devices for storing instructions and data. Generally, a CPU can receive instructions and data from (and write data to) a memory. A computer can also include, or be operatively coupled to, one or more mass storage devices for storing data. In some implementations, a computer can receive data from, and transfer data to, the mass storage devices including, for example, magnetic, magneto optical disks, or optical disks. Moreover, a computer can be embedded in another device, for example, a mobile telephone, a personal digital assistant (PDA), a mobile audio or video player, a game console, a global positioning system (GPS) receiver, or a portable storage device such as a universal serial bus (USB) flash drive.

Computer readable media (transitory or non-transitory, as appropriate) suitable for storing computer program instructions and data can include all forms of permanent/non-permanent and volatile/non-volatile memory, media, and memory devices. Computer readable media can include, for example, semiconductor memory devices such as random access memory (RAM), read only memory (ROM), phase change memory (PRAM), static random access memory (SRAM), dynamic random access memory (DRAM), erasable programmable read-only memory (EPROM), electrically erasable programmable read-only memory (EEPROM), and flash memory devices. Computer readable media can also include, for example, magnetic devices such as tape, cartridges, cassettes, and internal/removable disks. Computer readable media can also include magneto optical disks and optical memory devices and technologies including, for example, digital video disc (DVD), CD ROM, DVD+/−R, DVD-RAM, DVD-ROM, HD-DVD, and BLU-RAY. The memory can store various objects or data, including caches, classes, frameworks, applications, modules, backup data, jobs, web pages, web page templates, data structures, database tables, repositories, and dynamic information. Types of objects and data stored in memory can include parameters, variables, algorithms, instructions, rules, constraints, and references. Additionally, the memory can include logs, policies, security or access data, and reporting files. The processor and the memory can be supplemented by, or incorporated in, special purpose logic circuitry.

Implementations of the subject matter described in the present disclosure can be implemented on a computer having a display device for providing interaction with a user, including displaying information to (and receiving input from) the user. Types of display devices can include, for example, a cathode ray tube (CRT), a liquid crystal display (LCD), a light-emitting diode (LED), and a plasma monitor. Display devices can include a keyboard and pointing devices including, for example, a mouse, a trackball, or a trackpad. User input can also be provided to the computer through the use of a touchscreen, such as a tablet computer surface with pressure sensitivity or a multi-touch screen using capacitive or electric sensing. Other kinds of devices can be used to provide for interaction with a user, including to receive user feedback including, for example, sensory feedback including visual feedback, auditory feedback, or tactile feedback. Input from the user can be received in the form of acoustic, speech, or tactile input. In addition, a computer can interact with a user by sending documents to, and receiving documents from, a device that is used by the user. For example, the computer can send web pages to a web browser on a user's client device in response to requests received from the web browser.

The term "graphical user interface," or "GUI," can be used in the singular or the plural to describe one or more graphical user interfaces and each of the displays of a particular graphical user interface. Therefore, a GUI can represent any graphical user interface, including, but not limited to, a web browser, a touch screen, or a command line interface (CLI) that processes information and efficiently presents the information results to the user. In general, a GUI can include a plurality of user interface (UI) elements, some or all associated with a web browser, such as interactive fields, pull-down lists, and buttons. These and other UI elements can be related to or represent the functions of the web browser.

Implementations of the subject matter described in this specification can be implemented in a computing system that includes a back end component, for example, as a data server, or that includes a middleware component, for example, an application server. Moreover, the computing system can include a front-end component, for example, a client computer having one or both of a graphical user interface or a Web browser through which a user can interact with the computer. The components of the system can be interconnected by any form or medium of wireline or wireless digital data communication (or a combination of data communication) in a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) (for example, using 802.11 a/b/g/n or 802.20 or a combination of protocols), all or a portion of the Internet, or any other communication system or systems at one or more locations (or a combination of communication networks). The network can communicate with, for example, Internet Protocol (IP) packets, frame relay frames, asynchronous transfer mode (ATM) cells, voice, video, data, or a combination of communication types between network addresses.

The computing system can include clients and servers. A client and server can generally be remote from each other and can typically interact through a communication network. The relationship of client and server can arise by virtue of computer programs running on the respective computers and having a client-server relationship. Cluster file systems can be any file system type accessible from multiple servers for read and update. Locking or consistency tracking may not be necessary since the locking of exchange file system can be done at application layer. Furthermore, Unicode data files can be different from non-Unicode data files.

While this specification contains many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations, and it should be understood that the described program components and systems can generally be integrated together in a single software product or packaged into multiple software products.

Accordingly, the previously described example implementations do not define or constrain the present disclosure. Other changes, substitutions, and alterations are also possible without departing from the spirit and scope of the present disclosure.

Furthermore, any claimed implementation is considered to be applicable to at least a computer-implemented method; a non-transitory, computer-readable medium storing computer-readable instructions to perform the computer-implemented method; and a computer system comprising a computer memory interoperably coupled with a hardware processor configured to perform the computer-implemented method or the instructions stored on the non-transitory, computer-readable medium.

Particular embodiments of the subject matter have been described. Other embodiments are within the scope of the following claims. For example, the actions recited in the claims can be performed in a different order and still achieve desirable results. As one example, some processes depicted in the accompanying figures do not necessarily require the particular order shown, or sequential order, to achieve desirable results.

What is claimed is:

1. A computer-implemented method for petro-steering, the method comprising:
    obtaining, with one or more hardware processors, rock fabric data using petrography, X-Ray diffraction (XRD), and X-Ray fluorescence (XFD);
    integrating, with the one or more hardware processors, rock fabric data with dynamic productivity data in real time to identify patterns between the rock fabric data and dynamic productivity data, wherein a gas gain of the dynamic productivity data increases when a lateral well penetrates productive intervals; and
    predicting, with the one or more hardware processors, gas rates and steering values in drilled intervals of under-balanced coiled tubing wells based on the patterns; and
    petro-steering, using the steering values, across laterals of the underbalanced coiled tubing wells at the productive intervals based on the predicted gas rates to maximize reservoir contact within productive intervals during drilling.

2. The computer-implemented method of claim 1, wherein patterns are associations between geochemistry, mineralogy and gas flow rates.

3. The computer-implemented method of claim 1, wherein rock fabric data comprises elements and ratios generated by X-Ray Fluorescence analysis, wherein the gas rates are predicted according to the elements and ratios.

4. The computer-implemented method of claim 1, wherein rock fabric data comprises mineral identification using X-Ray diffraction analysis.

5. The computer-implemented method of claim 1, wherein the rock fabric data is static data that is compared to the dynamic productivity data to determine an accuracy of the dynamic productivity data.

6. The computer-implemented method of claim 1, further comprising guiding drilling operations to locations corresponding to a highest predicted gas rate for each location.

7. The computer-implemented method of claim 1, wherein the patterns between the rock fabric data and dynamic productivity data are identified using a trained machine learning model.

8. A system, comprising:
one or more memory modules;
one or more hardware processors communicably coupled to the one or more memory modules, the one or more hardware processors configured to execute instructions stored on the one or more memory modules to perform operations comprising:
obtaining rock fabric data using petrography, X-Ray diffraction (XRD), and X-Ray fluorescence (XFD);
integrating rock fabric data with dynamic productivity data in real time to identify patterns between the rock fabric data and dynamic productivity data, wherein a gas gain of the dynamic productivity data increases when a lateral well penetrates productive intervals; and
predicting gas rates and steering values in drilled intervals of underbalanced coiled tubing wells based on the patterns; and
petro-steering across laterals of the underbalanced coiled tubing wells at the productive intervals based on the predicted gas rates and steering values to maximize reservoir contact within productive intervals during drilling.

9. The system of claim 8, wherein patterns are associations between geochemistry, mineralogy and gas flow rates.

10. The system of claim 8, wherein rock fabric data comprises elements and ratios generated by X-Ray Fluorescence analysis, wherein the gas rates are predicted according to the elements and ratios.

11. The system of claim 8, wherein rock fabric data comprises mineral identification using X-Ray diffraction analysis.

12. The system of claim 8, wherein the rock fabric data is static data that is compared to the dynamic productivity data to determine an accuracy of the dynamic productivity data.

13. The system of claim 8, further comprising guiding drilling operations to locations corresponding to a highest predicted gas rate for each location.

14. The system of claim 8, wherein the patterns between the rock fabric data and dynamic productivity data are identified using a trained machine learning model.

15. An apparatus comprising a non-transitory, computer readable, storage medium that stores instructions that, when executed by at least one processor, cause the at least one processor to perform operations comprising:
obtaining rock fabric data using petrography and geochemical analysis using X-Ray diffraction (XRD) and X-Ray fluorescence (XFD);
integrating rock fabric data with dynamic productivity data in real time to identify patterns between the rock fabric data and dynamic productivity data, wherein a gas gain of the dynamic productivity data increases when a lateral well penetrates productive intervals; and
predicting gas rates and steering values in drilled intervals of underbalanced coiled tubing petro-steering, using the steering values, across laterals of the underbalanced coiled tubing wells at the productive intervals based on the predicted gas rates to maximize reservoir contact within productive intervals during drilling.

16. The apparatus of claim 15, wherein patterns are associations between geochemistry, mineralogy and gas flow rates.

17. The apparatus of claim 15, wherein rock fabric data comprises elements and ratios generated by X-Ray Fluorescence analysis, wherein the gas rates are predicted according to the elements and ratios.

18. The apparatus of claim 15, wherein rock fabric data comprises mineral identification using X-Ray diffraction analysis.

* * * * *

UNITED STATES PATENT AND TRADEMARK OFFICE
CERTIFICATE OF CORRECTION

PATENT NO. : 12,065,929 B2
APPLICATION NO. : 17/647814
DATED : August 20, 2024
INVENTOR(S) : Ferney Geovany Moreno Sierra et al.

It is certified that error appears in the above-identified patent and that said Letters Patent is hereby corrected as shown below:

In the Claims

Column 15, Claim 8, delete Lines 22-26 "petro-steering across laterals...during drilling." insert
-- petro-steering, using the steering values, across laterals of the underbalanced coiled tubing wells at the productive intervals based on the predicted gas rates to maximize reservoir contact within productive intervals during drilling. --.

Column 16, Claim 15, Line, 22, after "tubing" insert -- wells based on the patterns; and --.

Column 16, Claim 15, Line, 22, before "petro-steering" insert paragraph.

Signed and Sealed this
Twenty-ninth Day of April, 2025

Coke Morgan Stewart
*Acting Director of the United States Patent and Trademark Office*